(12) United States Patent
Sargeant

(10) Patent No.: US 9,474,575 B2
(45) Date of Patent: Oct. 25, 2016

(54) SYSTEM AND METHOD FOR UV TACKING AN IMPLANT

(75) Inventor: Timothy Sargeant, Guilford, CT (US)

(73) Assignee: Covidien LP, Mansfield, MA (US)

( * ) Notice: Subject to any disclaimer, the term of this patent is extended or adjusted under 35 U.S.C. 154(b) by 586 days.

(21) Appl. No.: 13/423,316

(22) Filed: Mar. 19, 2012

(65) Prior Publication Data

US 2012/0271290 A1 Oct. 25, 2012

Related U.S. Application Data

(60) Provisional application No. 61/478,154, filed on Apr. 22, 2011.

(51) Int. Cl.
| | |
|---|---|
| *A61B 18/18* | (2006.01) |
| *A61F 2/00* | (2006.01) |
| *A61B 17/29* | (2006.01) |
| *A61B 18/14* | (2006.01) |
| *A61B 17/00* | (2006.01) |

(52) U.S. Cl.
CPC ............. *A61B 18/18* (2013.01); *A61B 17/29* (2013.01); *A61F 2/0063* (2013.01); *A61B 18/1442* (2013.01); *A61B 2017/005* (2013.01); *A61B 2017/2926* (2013.01); *A61B 2018/1807* (2013.01); *A61F 2210/0085* (2013.01); *A61F 2220/005* (2013.01); *A61F 2220/0008* (2013.01)

(58) Field of Classification Search
CPC ................................................. A61B 18/1442
USPC ................................................. 606/2; 607/88
See application file for complete search history.

(56) References Cited

U.S. PATENT DOCUMENTS

| | | | |
|---|---|---|---|
| 4,273,110 | A | 6/1981 | Groux |
| 5,851,218 | A | 12/1998 | Lev |
| 6,709,128 | B2 | 3/2004 | Gordon et al. |
| 6,981,867 | B2 | 1/2006 | Cao |
| 7,182,597 | B2 | 2/2007 | Gill et al. |
| 7,273,369 | B2 | 9/2007 | Rosenblood et al. |
| 7,332,689 | B2 | 2/2008 | Mertens et al. |
| 7,427,262 | B2 | 9/2008 | Bonningue et al. |
| 7,677,888 | B1 | 3/2010 | Halm |
| 7,722,528 | B2 | 5/2010 | Arnal et al. |
| 7,753,936 | B2 | 7/2010 | Voegele et al. |
| 7,799,039 | B2 * | 9/2010 | Shelton et al. ............. 606/142 |

(Continued)

FOREIGN PATENT DOCUMENTS

WO WO2005/748141 A2 8/2005

OTHER PUBLICATIONS

European Search Report (6 pages) for EP12163852—date of mailing Aug. 13, 2012.

(Continued)

*Primary Examiner* — Aaron Roane

(57) ABSTRACT

A surgical instrument is provided including a handle portion and a body portion extending distally from the handle portion and defining a longitudinal axis. The surgical instrument also includes a grasper disposed at a distal end of the body portion, the grasper including an ultraviolet (UV) light mechanism for performing UV tacking of an implant. The implant is positioned between the first and second jaw members of the grasper: (i) to be placed at a surgical site and (ii) to be exposed by a UV light emitted from the UV light mechanism such that the UV tacking of the implant to the surgical site is performed.

10 Claims, 6 Drawing Sheets

(56) References Cited

U.S. PATENT DOCUMENTS

| | | |
|---|---|---|
| 8,113,830 B2 | 2/2012 | Gill et al. |
| 2006/0085005 A1 | 4/2006 | Kenealy, III et al. |
| 2006/0195010 A1* | 8/2006 | Arnal et al. ............ 600/30 |
| 2006/0286137 A1 | 12/2006 | Sandhu et al. |
| 2007/0088193 A1 | 4/2007 | Omori et al. |
| 2008/0039854 A1 | 2/2008 | Rabiner |
| 2008/0114381 A1* | 5/2008 | Voegele et al. ............ 606/151 |
| 2008/0306333 A1 | 12/2008 | Chin |
| 2008/0319259 A1 | 12/2008 | Goto |
| 2009/0248060 A1 | 10/2009 | Schneider et al. |
| 2010/0012703 A1 | 1/2010 | Calabrese |
| 2010/0063500 A1 | 3/2010 | Muszala |
| 2012/0271290 A1 | 10/2012 | Sargeant |

OTHER PUBLICATIONS

Partial European Search Report dated Jul. 2, 2014 for EP 14 16 4481.
Chinese Office Action for Application No. 201210118762.2 dated Feb. 2, 2015.
Chinese Office Action for Application No. 20120118762.2 dated Aug. 27, 2015.

* cited by examiner

SYSTEM AND METHOD FOR UV TACKING AN IMPLANT

CROSS REFERENCE TO RELATED APPLICATION

The present application claims the benefit of and priority to U.S. Provisional Application Ser. No. 61/478,154, filed on Apr. 22, 2011, the entire contents of which are incorporated herein by reference.

BACKGROUND

1. Technical Field

The present disclosure relates to endoscopic surgical instruments. More particularly, the present disclosure relates to a system and method for ultraviolet (UV) tacking an implant via an endoscopic surgical instrument having a UV light source mechanism distally disposed.

2. Background of Related Art

Surgical instruments which include a tool assembly mounted on a distal end of a body portion of the surgical instrument for articulation are well known. Typically, such surgical instruments include articulation control mechanisms, which allow an operator to remotely articulate the tool assembly in relation to the body portion of a surgical instrument to allow the operator to more easily access, operate on, and/or manipulate tissue.

Such articulating tool assemblies have become desirable, especially in the endoscopic surgical procedures. In an endoscopic surgical procedure, the distal end of a surgical instrument is inserted through small incisions in the body to access a surgical site. Typically, an appropriately sized cannula, e.g., 5 mm, 10 mm, etc., is inserted through the body incision to provide a guide channel for accessing the surgical site. Because it is desirable to provide small body incisions, i.e., less scarring, reduced trauma to the patient, faster healing time, the tolerances between the surgical instrument and the inner diameter of the cannula are small.

Conventional articulating tool tips have limited functionality mainly due to mechanical design limitations of actuating mechanisms. Thus, it is desirable to provide an articulating surgical instrument, which includes an articulation mechanism that would provide a wider range of functions for the articulation tip.

SUMMARY

Accordingly, an improved surgical instrument is provided. The surgical instrument includes a handle portion and a body portion extending distally from the handle portion and defining a longitudinal axis. The surgical instrument also includes a grasper disposed at a distal end of the body portion, the grasper including an ultraviolet (UV) light mechanism for performing UV tacking of an implant.

In another exemplary embodiment, the grasper is an end effector assembly having a first jaw member and a second jaw member. The first and second jaw members are movable from a first position in spaced relation relative to one another to a second position where the first and second jaw members cooperate to grasp the implant therebetween.

In another exemplary embodiment, the implant is a mesh having a UV reactive polymeric coating. The mesh is positioned between the first and second jaw members: (i) to be placed at a surgical site and (ii) to be exposed by a UV light emitted from the UV light mechanism such that the UV tacking of the mesh to the surgical site is performed. The mesh includes one or more tack regions each having a polymer coating embedded therein, the polymer coating being chemically induced by a UV light of the UV light mechanism.

A mesh having a UV reactive polymeric coating suitable for some embodiments of the present invention is found in U.S. Provisional Application Ser. No. 61/348,896 filed on May 27, 2010, the entire contents of which are incorporated by reference herein. In other embodiments, polymers as disclosed above are applied directly to tissue and then used to affix the mesh to tissue when polymerized with UV light.

In another exemplary embodiment, tack regions may be a uniform coating of the mesh surface or may be distinct regions. In yet another exemplary embodiment, the tack regions are visually designated along a length of the mesh. In a further embodiment, the regions tacked by the instrument change color when subjected to UV light or pressure, indicating locations on the mesh that have been tacked.

The UV light mechanism may be positioned on a non-grasping portion of the grasper. However, the UV light mechanism may be positioned on at least one grasping portion of the grasper.

In yet another exemplary embodiment, the surgical instrument further includes at least one sensor adapted to continuously or intermittently monitor UV light emission from the UV light mechanism. Additionally, the surgical instrument may include a trigger mechanism positioned on the handle portion for selectively activating the UV light mechanism.

In another exemplary embodiment, an improved surgical instrument assembly is provided. The surgical instrument assembly includes a handle portion and a body portion extending distally from the handle portion. The surgical instrument assembly also includes an end effector assembly disposed at a distal end of the body portion, the end effector assembly including a light source for tacking a mesh in position at a surgical site.

In another exemplary embodiment a method of UV tacking a mesh at a surgical site is provided. The method includes the steps of providing a surgical instrument including an ultraviolet (UV) light mechanism for performing UV tacking of an implant; providing a mesh implant having a polymeric coating activated by UV light; endoscopically positioning the mesh over the surgical site; and selectively applying UV light emitted from the UV light source to the mesh to tack the mesh to the site The mesh may include a polymeric coating that is activated upon exposure from the UV light emitted from the UV light source.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein.

DETAILED DESCRIPTION

Figure 1A:
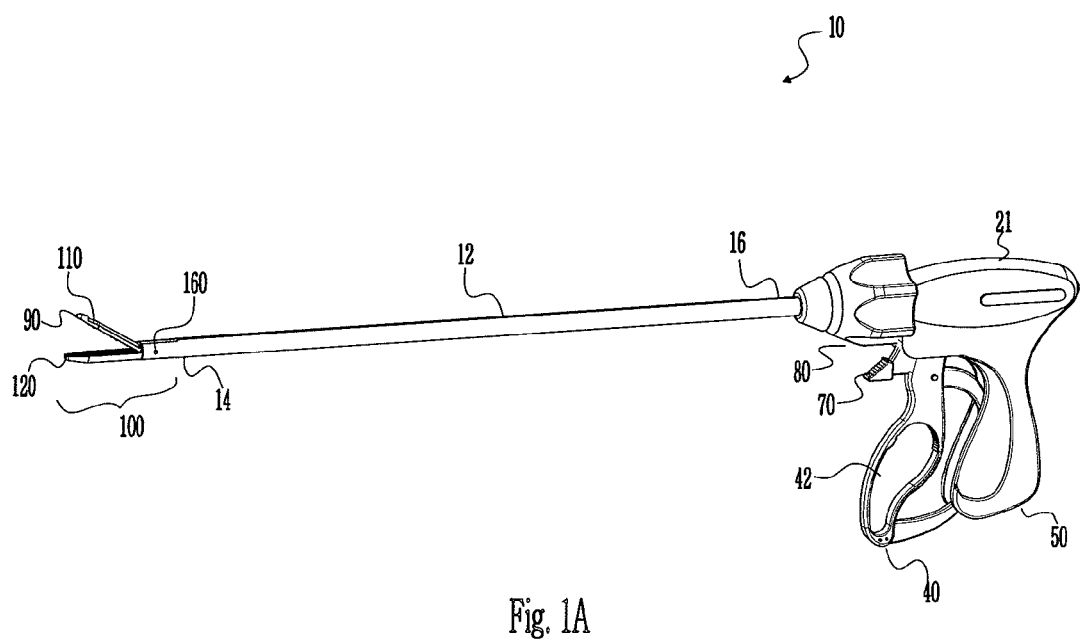
FIG. 1A is a perspective view of a surgical instrument in accordance with the present disclosure.

Embodiments of the presently disclosed apparatus will now be described in detail with reference to the drawings, in which like reference numerals designate identical or corresponding elements in each of the several views. As used herein, the term "distal" refers to that portion of the tool, or component thereof which is further from the user while the term "proximal" refers to that portion of the tool or component thereof which is closer to the user.

Figure 1B:
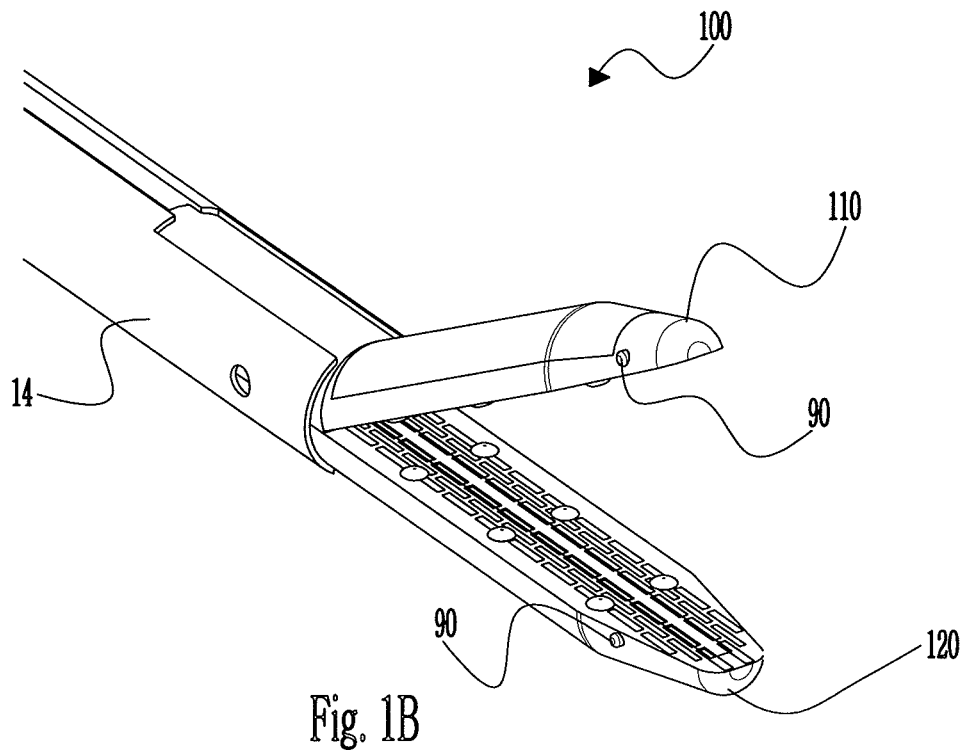
FIG. 1B is a perspective view of the end effector assembly of the surgical instrument of FIG. 1A, illustrating one or more ultraviolet (UV) light sources on a non-grasping portion of the end effector assembly, in accordance with the present disclosure.
Figure 1C:
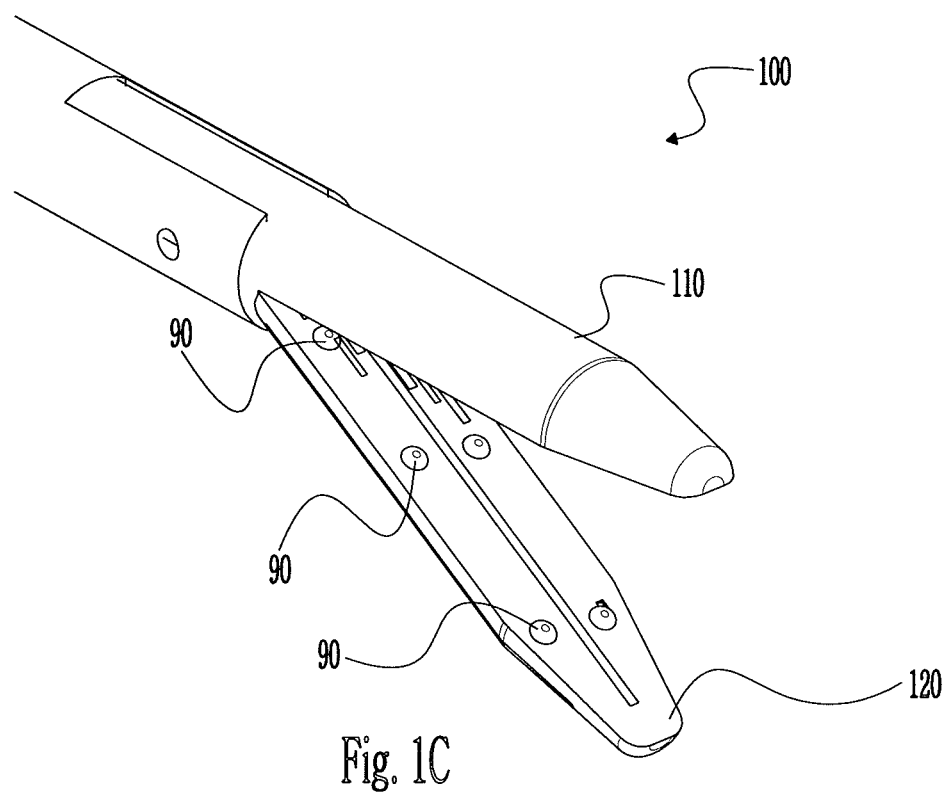
FIG. 1C is a perspective view of the end effector assembly of the surgical instrument of FIG. 1A, illustrating one or more UV light sources on grasping portions of the end effector assembly, in accordance with the present disclosure.

Referring to FIGS. 1A-1C, a surgical system for use in a surgical procedure, e.g., a minimally invasive procedure is illustrated.

FIG. 1A shows a surgical instrument 10 according to the present disclosure. More particularly, surgical instrument 10 generally includes a housing 21, a handle assembly 40, a rotating assembly 80, and a trigger assembly 70, which mutually cooperate with the end effector assembly 100 to grasp and treat tissue. Such a grasping instrument 10 is further exemplified by laparoscopic grasping instruments such as Covidien order codes 173030, 174317, 174001 and 174233.

The surgical instrument 10 also includes a shaft 12, which has a distal end 14 that mechanically engages the end effector assembly 100 and a proximal end 16 that mechanically engages the housing 21 proximate the rotating assembly 80. Handle assembly 40 includes a fixed handle 50 and a movable handle 42. Handle 42 moves relative to the fixed handle 50 to actuate the end effector assembly 100 and enable a user to grasp and manipulate tissue.

The end effector assembly 100 includes opposing jaw members 110, 120. The jaw members 110, 120 are activated by using a drive assembly (not shown) enclosed within the housing 21. The drive assembly cooperates with the movable handle 42 to impart movement of the jaw members 110, 120 from the open position to the clamping or closed position.

The surgical instrument 10 also includes a rotating assembly 80 mechanically associated with the shaft 12 and the drive assembly (not shown). Movement of the rotating assembly 80 imparts similar rotational movement to the shaft 12 which, in turn, rotates the end effector assembly 100.

As best seen with respect to FIG. 1A, the end effector assembly 100 attaches to the distal end 14 of shaft 12. The jaw members 110, 120 are pivotable about a pivot 160 from the open to closed positions upon relative reciprocation, i.e., longitudinal movement, of the drive assembly (not shown). It is envisioned that the surgical instrument 10 may be designed such that it is fully or partially disposable depending upon a particular purpose or to achieve a particular result. For example, end effector assembly 100 may be selectively and releasably engageable with the distal end 14 of the shaft 12 and/or the proximal end 16 of the shaft 12 may be selectively and releasably engageable with the housing 21 and handle assembly 40. In either of these two instances, the surgical instrument 10 may be either partially disposable or reposable, such as where a new or different end effector assembly 100 or end effector assembly 100 and shaft 12 are used to selectively replace the old end effector assembly 100 as needed.

Additionally, FIG. 1A illustrates a UV light source 90 (or UV light mechanism) disposed at the distal end of the first jaw 110. The UV light source 90 is better seen in FIGS. 1B and 1C, which illustrate the end effector assembly 100. FIG. 1B illustrates one or more UV light sources 90 on the first jaw 110 and the second jaw 120 (i.e., the non-grasping portions of the jaws 110, 120). FIG. 1C illustrates one or more UV light sources 90 on the grasping portions of the second jaw 120. One skilled in the art may contemplate using a number of different UV light sources on one jaw or on both jaws and may contemplate positioning such UV light sources on or about any desired portion(s) of the end effector assembly 100.

Figure 3A:
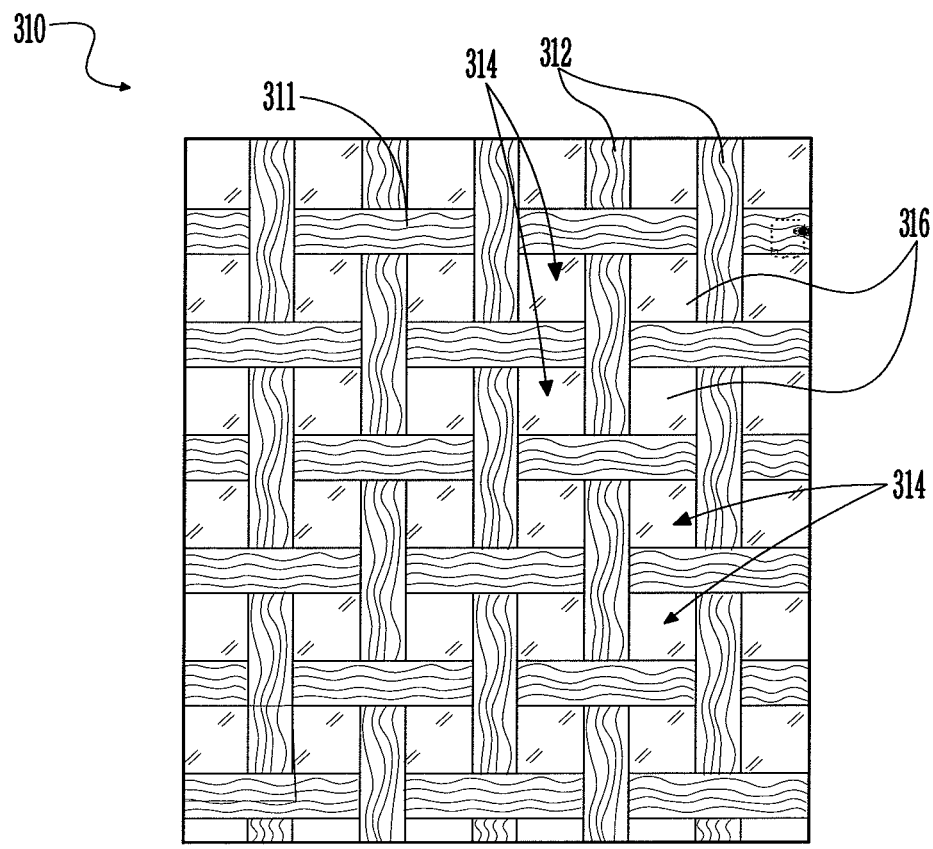
FIG. 3A is a perspective view of the mesh, in accordance with the present disclosure.
Figure 3B:
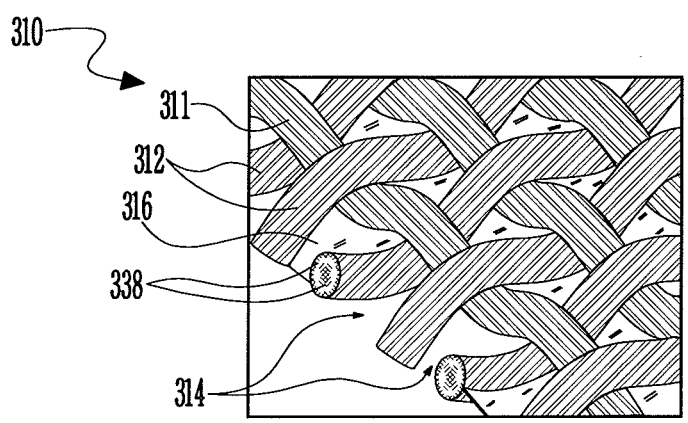
FIG. 3B is a perspective cross-sectional view of the mesh of FIG. 3A, in accordance with the present disclosure.

In operation, the jaw members 110, 120 are positioned in the vicinity of an incision of a surgical site for placement of an implant or mesh (see FIGS. 3A and 3B). The light sources 90 positioned on the first and second jaws 110, 120 (see FIG. 1B) are triggered to emit UV light to activate an adhesive on the implant or mesh to permanently secure the implant or mesh to the incision of the surgical site. The adhesive may be a UV activated adhesive. Thus, the surgical instrument 10 may perform a full cure to permanently attach or tack the implant or mesh by using the UV light source 90 to activate UV adhesive sprayed on the implant or mesh. A less than full cure for temporarily securing the implant may be achieved by applying a lower energy of UV light.

Energy is transmitted to the implant or mesh from one or more energy transmission devices such as a laser or lasers. In at least one embodiment, the laser is a UV laser, however in some alternative embodiments the laser may be an IR laser, diode laser, $CO_2$, visible light, or any other form of laser device or combinations thereof. One skilled in the art may contemplate using a plurality of different forms of energy in order to tack the implant or mesh to the incision of the surgical site. For example, one skilled in the art may use thermal energy, microwave energy, chemical energy, and/or ultrasonic energy or a combination thereof.

Figure 2A:
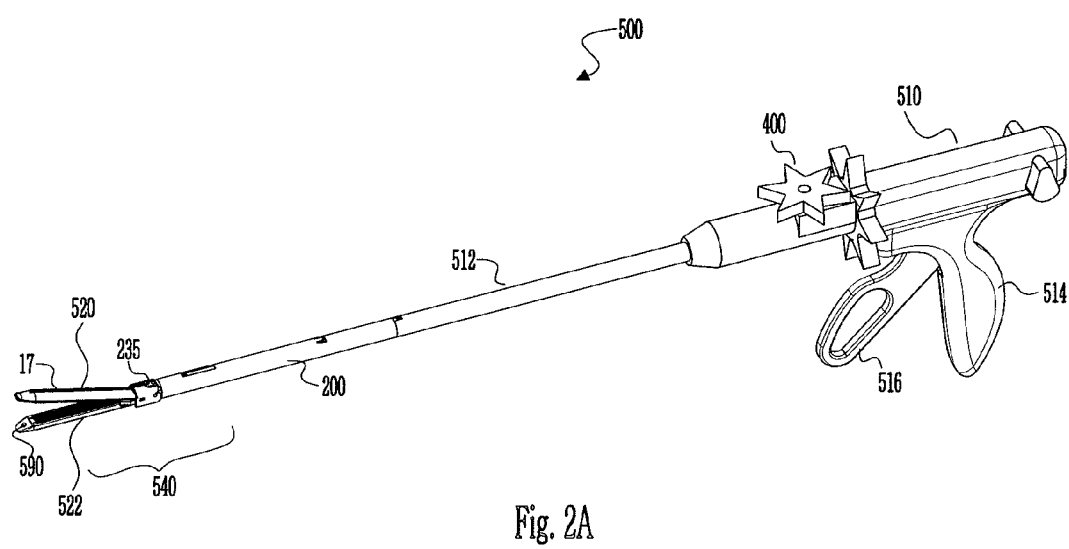
FIG. 2A is a perspective view of another surgical stapling instrument in accordance with the present disclosure.

Referring to FIG. 2A, a perspective view of another surgical stapling instrument 500 in accordance with the present disclosure is presented.

In FIG. 2A, surgical instrument 500 includes a handle portion 510, a body portion 512, and a disposable loading unit ("DLU") 540. Handle portion 510 includes a stationary handle 514 and a movable handle or trigger 516. Movable handle 516 is movable in relation to stationary handle 514 to advance a control rod 520 (not shown), which projects from the distal end of body portion 512. Alternately, other surgical instruments may be used with DLU 540 to perform endoscopic surgical procedures. The surgical instrument 500 also includes an articulation mechanism 400 for articulating a tool assembly 17 of the DLU 540. The tool assembly 17 may include a first jaw 520 and a second jaw 522.

DLU 540 includes a tool assembly 17, a proximal body portion 200 and a mounting assembly 235. Body portion 200 has a proximal end adapted to releasably engage the distal end of a surgical instrument 500. Mounting assembly 235 is pivotally secured to a distal end of body portion 200 and is fixedly secured to a proximal end of tool assembly 17. Pivotal movement of mounting assembly 235 about an axis perpendicular to a longitudinal axis of body portion 200 effects articulation of tool assembly 17 between a non-articulated position in which the longitudinal axis of tool assembly 17 is aligned with the longitudinal axis of body portion 200 and an articulated position in which the longitudinal axis of tool assembly 17 is disposed at an angle to the longitudinal axis of body portion 200.

Figure 2B:
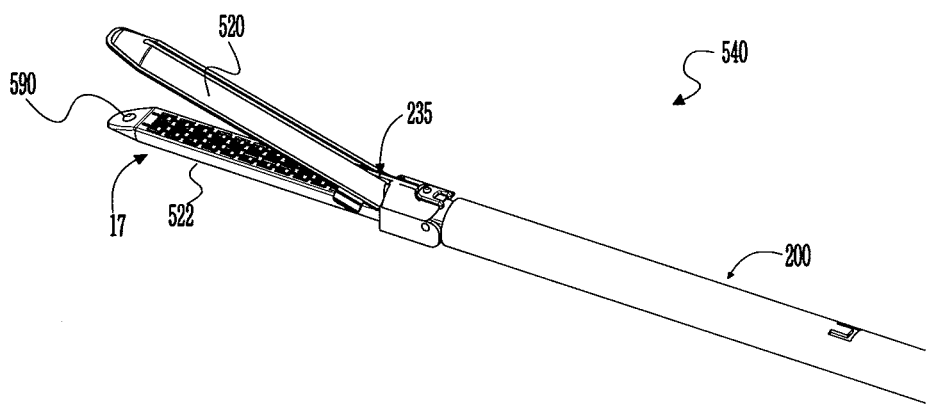
FIG. 2B is a perspective view of the end effector assembly of the surgical instrument of FIG. 2A, illustrating one or more UV light sources on a non-grasping portion of the end effector assembly, in accordance with the present disclosure.
Figure 2C:
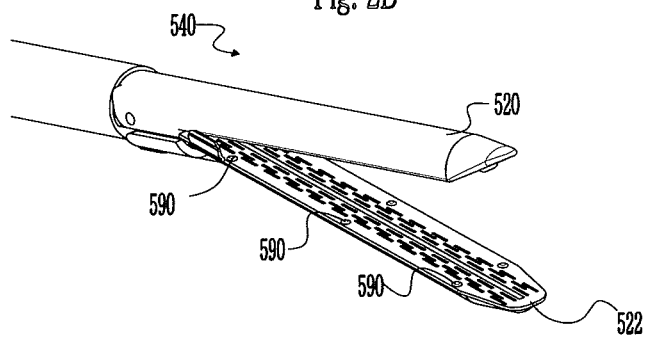
FIG. 2C is a perspective view of the end effector assembly of the surgical instrument of FIG. 2A, illustrating one or more UV light sources on grasping portions of the end effector assembly, in accordance with the present disclosure.

Additionally, the surgical instrument 500 includes a UV light source 590 (or UV light mechanism) disposed at the distal end of the tool assembly 17. The UV light source 590 is better seen in FIGS. 2B and 2C, which illustrate the tool assembly 17. FIG. 2B illustrates one or more UV light sources 590 on the lower jaw (i.e., the non-grasping portion of the tool assembly 17). FIG. 2C illustrates one or more UV light sources 590 on the grasping portions of the tool assembly 17. One skilled in the art may contemplate using a number of different UV light sources on one jaw or on both jaws and may contemplate positioning such UV light sources on or about any desired portion(s) of the tool assembly 17.

Referring to FIGS. 2B and 2C, perspective views of the tool assembly 17 of the surgical instrument 500 of FIG. 2A, illustrating one or more UV light sources 590 on a non-grasping portion and a grasping portion of the tool assembly 17, respectively, in accordance with the present disclosure is presented.

In operation, the jaw members 520, 522 are positioned in the vicinity of an incision of a surgical site for placement of an implant or mesh (see FIGS. 3A and 3B). The light sources 590 positioned on the second jaw 520 (see FIG. 2C) are triggered to emit UV light to activate an adhesive on the implant or mesh to permanently secure the implant or mesh to the incision of the surgical site. The adhesive may be a UV activated adhesive. Thus, the surgical instrument 500 may perform a full cure to permanently attach or tack the implant or mesh by using the UV light source 590 to activate UV adhesive sprayed on the implant or mesh.

Referring to FIG. 3A, a perspective view of the mesh 310, in accordance with the present disclosure is presented, whereas referring to FIG. 3B a perspective cross-sectional view of the mesh 310 of FIG. 3A, in accordance with the present disclosure is presented.

The surgical mesh 310 (or implant) is suitable for surgical repair of hernias and other surgical procedures requiring reinforcement or repair of soft tissue, such as muscle or wall tissue defects, pelvic organ prolapse, and urinary incontinence, for example. The mesh 310 of the present disclosure may be in the form of sheets, patches, slings, suspenders, and other implants and composite materials such as pledgets, buttresses, wound dressings, drug delivery devices, and the like. The present surgical mesh 310 may be implanted using open surgery or by a laparoscopic procedure.

The surgical mesh 310 may be fabricated from monofilament and/or multifilament yarns 312, which may be made of any suitable biocompatible material. Suitable materials from which the mesh 310 may be made should have the following characteristics: sufficient tensile strength to support tissue; sufficiently inert to avoid foreign body reactions when retained in the body for long periods of time; easily sterilized to prevent the introduction of infection when the mesh 310 is implanted in the body; and sufficiently strong to avoid tearing of portions thereof.

Referring now to FIGS. 3A and 3B, the mesh 310 is illustrated including a porous mesh substrate 311. The substrate 311 may be formed from fibers, filaments, threads or yarns 312 defining a plurality of pores 314 therebetween. The yarns 312 of the substrate 311 may be made up of multiple filaments 338 (see FIG. 3B). The pores 314 may include one or more intra-pore films 316. The intra-pore films 316 of the present disclosure are non-contiguous with respect to one another, with each intra-pore film 316 being located in a single pore 314 of the porous substrate 311. In embodiments, multiple intra-pore films 316 may also be formed within each of the pores 314 of the substrate 311. The term "non-contiguous" as used herein, is used to denote one or more films 316 that are wholly contained within a corresponding pore 314 and are not in physical contact with another intra-pore film 316 of any other pore 314, as compared to a conventional film-coated porous substrate in which the film stretches across multiple pores. The intra-pore films 316 are solely contained within the pores of the substrate. The intra-pore film does not span across the yarns 312 of the substrate. The intra-pore films 316 are non-contiguous and are not bridged together by applying a film over the entire substrate, but rather, the intra-pore films 316 are created at discrete locations, within the individual pores.

The intra-pore films 316 may be formed at any plane within the pores 314 relative to the plane of the substrate 311 such that the intra-pore film 316 does not contact any adjacent intra-pore film 316. In embodiments, the intra-pore film 316 may be textured, smooth and/or porous.

In a preferred embodiment, the yarns 312 may be sprayed with a UV polymer adhesive that is activated when a UV light source 90, 590 (see FIGS. 1A-2C) is placed in the proximity of the yarns 312 of the mesh 310.

As illustrated in FIG. 3A, not every pore 314 includes an intra-pore film. In certain embodiments, the pores including intra-pore films may be from about 10% to about 95% of the pores. In further embodiments, about 15% to about 90% of the pores of the substrate 311 include at least one intra-pore film. In other embodiments, from about 25% to about 75% of the pores of the substrate 311 include at least one intra-pore film. In other embodiments, all of the pores of the substrate 311 may include an intra-pore film.

The substrate 311 may include at least a center and a periphery. In embodiments where less than 100% of the pores of the substrate 311 include intra-pore films, the location of the intra-pore films may be random or patterned. For example, the pores of the substrate 311 that include the intra-pore films may be solely disposed in the center of the substrate 311 or the pores that include the intra-pore films may be solely disposed on the periphery of the substrate. In embodiments, the location of intra-pore films may be varied (e.g., random, patterned, etc.) depending upon the intended use of the substrate 311. The intra-pore films may form a discontinuous layer covering intermittent portions of the surface of the substrate 311. In one example, the intra-pore films may form a discontinuous layer on the surface of the substrate 311, wherein the porosity of the substrate 311 is maintained by the discontinuous layer of the intra-pore films.

Each intra-pore film 316 of a substrate 311 may be made from the same materials or different materials. In particular, one or more of the intra-pore films 316 may be formed from one material, while one or more different intra-pore films 316 may be formed from another material. The intra-pore film 316 may be permanent (e.g., non-bioabsorbable), biodegradable, or may be formed from any suitable combination of natural, synthetic, biodegradable and non-biodegradable materials. In the present application, the terms "biodegradable," "bioresorbable," and "bioabsorbable" are used interchangeably and are intended to mean the characteristic according to which an implant and/or a material is resorbed by biological tissues and the surrounding fluids, and disappears in vivo after a given period of time. The time period may vary, from about one minute to about several months or more, depending on the chemical nature of the implant and/or of the material utilized to form the implant.

In alternate embodiments, the substrate may include intra-pore films that have a varying degradation rates, such that some of the intra-pore films degrade at a rate different from that of other intra-pore films. The type of material used to form the film, concentration of the material, and structure of the film, are some factors which may affect the degradation time of the film.

In some embodiments, the yarns 312 include at least two filaments, which may be arranged to create openings therebetween, the yarns 312 also being arranged relative to each other to form openings in the mesh 310. Alternatively, the mesh 310 may be formed from a continuous yarn 312 that is arranged in loops that give rise to the openings in the mesh 310. The use of a mesh 310 having yarns spaced apart in accordance with the present disclosure has the advantage of reducing the foreign body mass that is implanted in the body, while maintaining sufficient tensile strength to securely support the defect and tissue being repaired by the mesh 310. Moreover, the openings of the mesh 310 of the present disclosure may be sized to permit fibroblast through-growth and ordered collagen laydown, resulting in integration of the mesh 310 into the body. Thus, the spacing between the yarns 312 may vary depending on the surgical application and desired implant characteristics as envisioned by those skilled in the art.

All the above alternate embodiments of the mesh 310 may include one or more yarns 312 and/or pores 314 having UV adhesive sprayed thereon during manufacturing for being activated by any type of UV light source 90, 590 of any type of surgical instrument/system 10, 500. Therefore, the mesh 310 may be any type of biodegradable polymeric coating having UV properties for interacting with UV light sources 90, 590.

It may desirable to reposition the mesh 310. In that instance, the mesh adhesive may be initially tacky to allow repositioning of the mesh. Alternatively, the mesh adhesive may be partially polymerized by a relatively briefer application or lower energy application of UV light to achieve tackiness or a light bonding to tissue. In any case, when mesh is repositioned after application of UV light, it is desirable to know what regions of the mesh 310 have been originally subjected to UV light to enable applying the light to an uncured region of the mesh. This may be aided by marking certain adjacent zones of the mesh 310 with numeric or alphabetic sequences such as A, B, C so that the surgeon may locate the mesh positions of a first bonding attempt during repositioning. Further, the mesh 310 may be treated with a heat or pressure reactant dye to display a visual indication that UV light has been applied or that the jaws of grasping instrument 10 have applied pressure indicative of bonding to the mesh.

Figure 4A:
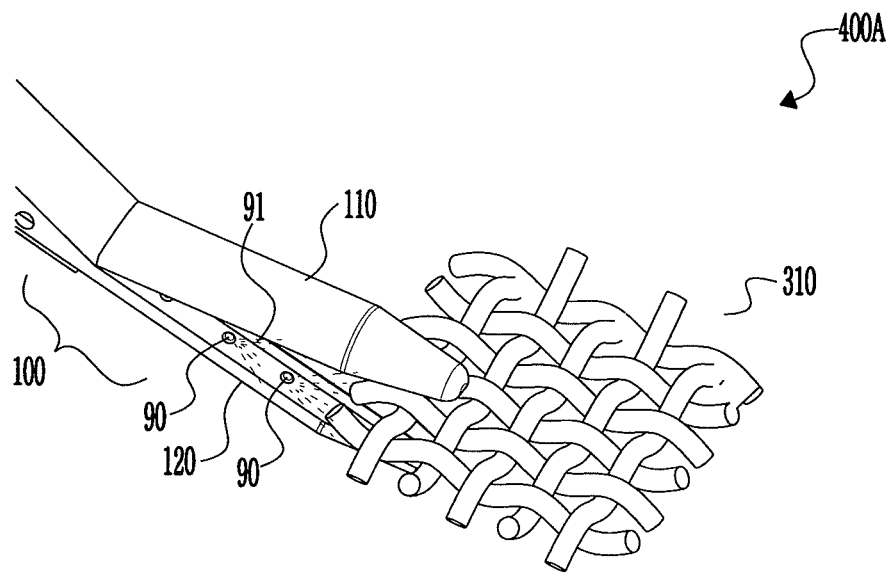
FIG. 4A is a perspective view of the surgical instrument of FIG. 1A grasping the mesh of FIG. 3A, in order to apply UV light via the one or more UV light sources to the mesh, in accordance with the present disclosure.

Referring to FIG. 4A, a perspective view 400A of the surgical instrument 10 of FIG. 1A grasping the mesh 310 of FIG. 3A, in order to apply UV light via the one or more UV light source 90 to the mesh 310, in accordance with the present disclosure is presented.

Figure 4B:
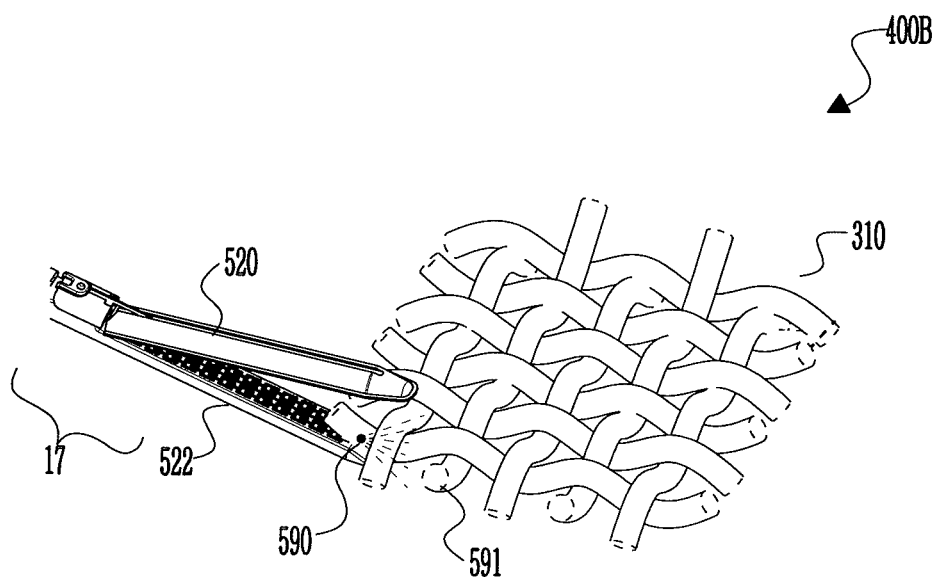
FIG. 4B is a perspective view of the surgical instrument of FIG. 2A grasping the mesh of FIG. 3A, in order to apply UV light via the one or more UV light sources to the mesh, in accordance with the present disclosure.

Referring to FIG. 4B, a perspective view 400B of the surgical instrument 500 of FIG. 2A grasping the mesh 310 of FIG. 3A, in order to apply UV light via the one or more UV light sources 590 to the mesh 310, in accordance with the present disclosure is presented.

In operation, the mesh 310 is positioned between the first and second jaw members 110, 120 of surgical instrument 10: (i) to be placed at a surgical site and (ii) to be exposed by a UV light 91 emitted from the UV light mechanism 90, such that the UV tacking of the mesh 310 to the surgical site is performed (see FIG. 4A). Similarly, the mesh 310 is positioned between the first and second jaw members 520, 522 of instrument 500: (i) to be placed at a surgical site and (ii) to be exposed by a UV light 591 emitted from the UV light mechanism 590 such that the UV tacking of the mesh 310 to the surgical site is performed (see FIG. 4B).

The mesh 310 may include one or more tack regions each having a polymer coating embedded therein, the polymer coating being chemically induced by a UV light of the UV light mechanism 90, 590. Additionally, the one or more tack regions may have a thickness that is greater than a thickness of the mesh 310. Alternatively, the one or more tack regions may be positioned substantially equidistant from each other along a length of the mesh 310.

Therefore, in accordance with the present disclosure, the method of UV tacking a mesh includes the step of applying energy to a handle portion of a surgical instrument having a body portion extending distally therefrom a handle portion. The next steps may be positioning an end effector assembly at a distal end of the body portion and incorporating a UV light source at the end effector assembly. A user may then selectively apply a UV light emitted from the UV light source to the mesh and UV-tack the mesh to the surgical site. The mesh may include a biodegradable polymeric coating that is activated upon exposure from the UV light emitted from the UV light source.

In another exemplary embodiment, at least one sensor may be adapted to continuously or intermittently monitor UV light emission from the UV light mechanism.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of presently disclosed embodiments. Thus the scope of the embodiments should be determined by the appended claims and their legal equivalents, rather than by the examples given.

Persons skilled in the art will understand that the devices and methods specifically described herein and illustrated in the accompanying drawings are non-limiting exemplary embodiments. The features illustrated or described in connection with one exemplary embodiment may be combined with the features of other embodiments. Such modifications and variations are intended to be included within the scope of the present disclosure. As well, one skilled in the art will appreciate further features and advantages of the present disclosure based on the above-described embodiments.

The invention claimed is:

1. A surgical instrument comprising:
   a handle portion;
   a body portion extending distally from the handle portion and defining a longitudinal axis; and
   an end effector disposed at a distal end of the body portion, the end effector including:
   grasping portions having first surfaces adapted to contact one of tissue or mesh and second surfaces that are separate from the first surfaces;
   a first plurality of ultraviolet (UV) mechanisms positioned on the first surfaces; and
   a second plurality of UV mechanisms positioned on the second surfaces, the first and second plurality of UV mechanisms configured to perform UV tacking of a mesh including one or more tack regions each having a polymeric coating activated by UV light emitted directly on the mesh by the first and second pluralities of UV mechanisms, wherein each UV mechanism of the first and second pluralities of UV mechanisms is a discrete component and capable of emitting UV light.

2. The surgical instrument according to claim 1, wherein the grasping portions of the end effector include a first jaw member and a second jaw member.

3. The surgical instrument according to claim 2, wherein the first and second jaw members are movable from a first position in spaced relation relative to one another to a second position where the first and second jaw members cooperate to grasp the mesh therebetween.

4. The surgical instrument according to claim 1, wherein a portion of a mesh including one or more intra-pore films is positioned between the grasping portions of the end effector and is capable of being placed at a surgical site to be exposed by the UV light emitted from the first and second pluralities of UV mechanisms.

5. The surgical instrument according to claim 1, wherein a portion of a mesh including one or more tack regions having visual location designations is positioned between the grasping portions of the end effector and is capable of being placed at a surgical site to be exposed by the UV light emitted from the first and second pluralities of UV mechanisms.

6. The surgical instrument according to claim 1, wherein a portion of a mesh including one or more tack regions that are visually altered by the UV light emitted from the first and second plurality of UV mechanisms is positioned between the grasping portions of the end effector and is capable of being placed at a surgical site to be exposed by the UV light emitted from the first and second pluralities of UV mechanisms.

7. The surgical instrument according to claim 1, further comprising at least one sensor adapted to monitor the UV light emitted from the first and second pluralities of UV mechanisms.

8. The surgical instrument according to claim 1, further comprising a trigger mechanism positioned on the handle portion for selectively activating the first and second pluralities of UV mechanisms.

9. The surgical instrument according to claim 1, further comprising a control mechanism for activating each UV mechanism of the first and second pluralities of UV mechanisms.

10. A surgical instrument comprising:
    a handle portion;
    a body portion extending from the handle portion and defining a longitudinal axis; and
    an end effector disposed at a distal end of the body portion, the end effector including:
    grasping portions having first surfaces adapted to contact one of tissue or mesh and second surfaces that are adjacent to the first surfaces, the tissue or mesh defining a first area that is in contact with the first surfaces and a second area separate from the first area;
    a first plurality of ultraviolet (UV) mechanisms positioned on the first surfaces; and
    a second plurality of UV mechanisms positioned on the second surfaces, the first and second pluralities of UV mechanisms configured to perform UV tacking of a mesh including one or more tack regions each having a polymeric coating activated by UV light emitted directly on the mesh by the first and second pluralities of UV mechanisms, wherein the first plurality of UV mechanisms is configured to emit UV light directly on the first area and the second plurality of UV mechanisms is configured to emit UV light directly on the second area,
    wherein each UV mechanism of the first and second pluralities of UV mechanisms is a discrete component and capable of emitting UV light.

* * * * *